United States Statutory Invention Registration [19]

[11] Reg. Number: H504

Levitt et al.

[43] Published: Aug. 2, 1988

[54] PROCESS FOR THE PREPARATION OF ALKYL 3-CHLOROSULFONYLTHIOPHENE-2-CARBOXYLATE

[75] Inventors: George Levitt; Richard V. Pater, both of Wilmington, Del.

[73] Assignee: E. I. Du Pont de Nemours and Company, Wilmington, Del.

[21] Appl. No.: 707,622

[22] Filed: Mar. 7, 1985

Related U.S. Application Data

[63] Continuation-in-part of Ser. No. 613,783, May 24, 1984, abandoned.

[51] Int. Cl.[4] ..... C07D 333/32; C07D 333/34
[52] U.S. Cl. ..... 549/64
[58] Field of Search ..... 549/64

[56] References Cited

U.S. PATENT DOCUMENTS 2,623,050 12/1952 Graenacher et al. ..... 549/64
2,653,927 9/1953 Graenacher et al. ..... 549/64

OTHER PUBLICATIONS

Chemische Berichte, vol. 90 (1957) pp. 841–852, Meerwein et al.

*The Chemistry of Heterocyclic Compounds,* pp. 228–235, "Thiophene and its Derivatives".

Huddleston et al., J. Chem. Research, 1980, pp. 238–239.

Hentschel et al., J. Prakt. Chemie. 316, 5, 1974, pp. 878–880.

Bull. Soc. Chem. Fra., 1925, pp. 1437–1438.

*Primary Examiner*—John F. Terapane
*Assistant Examiner*—J. E. Thomas

[57] ABSTRACT

A process for preparation of chlorosulfonyl thiophene compounds comprising contacting a thiophenamine with sodium or potassium nitrite to produce a diazonium salt, then contacting said salt with sulfur dioxide and cuprous or cupric chloride, or bromide. Addition of gaseous HCl, concentrated $H_2SO_4$, or oleum to the diazotization mixture enhances yield.

9 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESS FOR THE PREPARATION OF ALKYL 3-CHLOROSULFONYLTHIOPHENE-2-CARBOXYLATE

RELATED APPLICATIONS

This application is a continuation-in-part of U.S. Ser. No. 613,783, filed May 24, 1984, now abandoned.

BACKGROUND OF THE INVENTION

Substituted alkyl 3-chlorosulfonylthiophene-2-carboxylates are of considerable interest in the preparation of pharmaceuticals and herbicides. U.S. Pat. No. 4,224,445 issued Sept. 23, 1980 to Hromatka et al. discloses the utility of these intermediates in the preparation of compounds possessing anti-inflammatory, analgesic, and antirheumatic activity. European Patent Application No. 30142 discloses herbicidal sulfonyl urea compounds derived from substituted alkyl 3-chlorosulfonylthiophene-2-carboxylates.

Therefore it is of great importance to develop economically attractive processes to substituted alkyl 3-chlorosulfonylthiophene-2-carboxylates that involve few chemical steps, with easy to carry out operations, and utilize inexpensive starting materials and reagents.

U.S. Pat. No. 4,230,873 issued Oct. 28, 1980 to Hromatka et al. discloses a multistep process leading to substituted alkyl 3-chlorosulfonylthiophene-2-carboxylates which involves converting the '3 hydroxythiophene-2-carboxylic acid methyl ester. This process, in addition to its many steps, is encumbered by the usage of large quantities of such reagents as $PCl_5$ and $SOCl_2$ which result in severe waste disposal problems.

SUMMARY OF THE INVENTION

This invention relates to a process for the preparation of compounds of Formula I

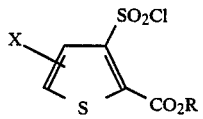

I wherein

R is $C_1$–$C_3$ alkyl; and

X is H, Cl, Br or $CH_3$.

The process comprises:

(a) contacting a thiophenamine of Formula II suspended in excess aqueous hydrochloric acid and a cosolvent selected from acetic, formic or propionic acid with sodium or potassium nitrite, optionally in the presence of a mineral acid booster selected from gaseous hydrochloric acid, concentrated sulfuric acid or oleum, to produce a diazonium salt of Formula III;

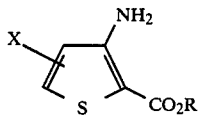

II

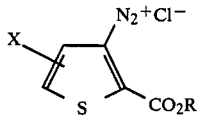

III and, (b) contacting a solution of the diazonium salt of Formula III with sulfur dioxide in the presence of cupric or cuprous chloride, or bromide, to produce said compound of Formula I.

When using readily available low-strength hydrochloric acid and water-wet thiophenamine of Formula II, it has been found that high yields of sulfonyl chloride I can be obtained and side-product formation minimized by the addition of a mineral acid booster, selected from gaseous hydrogen chloride, concentrated sulfuric acid or oleum, to the diazotization mixture.

Preferred for reasons of increased ease of operation and/or higher yield and/or greater purity of products are:

(1) The above process where the cosolvent is acetic acid and the concentration of aqueous hydrochloric acid is at least 35% by weight;

(2) The process of Preferred 1 where R is $CH_3$:

(3) The process of Preferred 2 where X is $CH_3$;

(4) The process of Preferred 2 where X is H;

(5) The process of Preferred 1 in which a mineral acid booster is present.

(6) The process of Preferred 5 in which the mineral acid booster is present in an amount of 0.1 to 3.5 moles of concentrated sulfuric acid per mole of diazonium salt;

(7) The process of Preferred 5 where the mineral acid boostez is present in the amount of 0.2 to 2.5 moles of concentrated sulfuric acid per mole of diazonium salt, R is $CH_3$ and X is H.

DETAILED DESCRIPTION OF THE INVENTION

It is well known in the art that various substituted anilines can be converted to the corresponding sulfonyl chlorides via a 2-step process of diazotization and $SO_2$-$CuCl_2$ decomposition:

$$Ar{-}NH_2 \xrightarrow[2.\ SO_2{-}CuCl_2]{1.\ HCl/NaNO_2} ArSO_2Cl \qquad (2)$$

wherein Ar is phenyl or a substituted phenyl moiety. A detailed description of such a process by H. Meerwein, G. Dittmar, R. Göllner, K. Hafner, F. Mensch an O. Steinfort can be found in Chemische Berichte, Vol. 90, 1957, pages 841–852.

However, it is not known in the art that a thiophenamine or a substituted thiophenamine can be converted to the corresponding thiophene sulfonyl chloride (Equation 3):

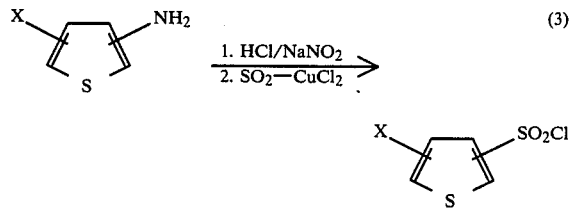

(3)

It has been found that such a conversion proceeds well When a thiophenamine of general Formula II is suspended in a mixture of excess concentrated hydrochloric acid (also referred to herein as aqueous hydrochloric acid) and a cosolvent selected from formic, acetic or propionic acid, optionally in the presence of a mineral-acid booster selected from hydrogen chloride, concentrated sulfuric acid or oleum, and the suspension is (a) contacted with an aqueous solution of sodium or potassium nitrite which produces a diazonium salt of general Formula III; and (b) the diazonium salt III so produced is contacted with cupric or cuprous chloride or bromide, in the presence of excess sulfur dioxide to give the desired thiophenesulfonyl chloride of general Formula I. The procedure outlined above, however, requires that the concentrated hydrochloric acid be at least 35 weight percent for the attainment of highest yields and low levels of side products. When inexpensive, low-strength (28–32 weight percent) hydrochloric acid and /or readily available water-wet thiophenamine are employed, the yields of thiophenesulfonyl chlorides decrease drastically. In addition, the sulfonyl chlorides have low purities, being contaminated with many side products among which the type represented by general Formula IV predominates:

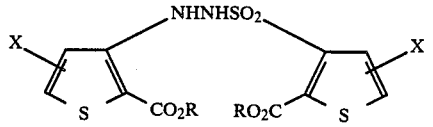

IV

This type of impurity is very difficult to remove from the corresponding thiophenesulfonyl chloride I.

In those instances, high yields of sulfonyl chloride I can be maintained and side-product formation can be minimized by the addition of hydrogen chloride, concentrated sulfuric acid or oleum to the diazotization mixture. Most preferred in achieving higher yield and-/or greater purity of products is the addition of concentrated sulfuric acid in the amount of 0.2 to 2.5 moles per mole of diazonium salt III.

The reactions of Equation 3 comprising our improved process can preferably be carried out by the following procedure:

To concentrated hydrochloric acid (35–38 weight percent) is added glacial acetic acid as cosolvent. The amount of the former is selected to provide approximately 5.0 molar equivalents of HCl per mole of the substrate thiophenamine. The amount of cosolvent acetic acid is selected to provide a stirrable slurry of the substrate thiophenamine.

If an inexpensive, lower-strength hydrochloric acid (28–32 weight percent) and/or water wet thiophenamine are used, concentrated sulfuric acid is added at this stage for reason of the convenience of mixing sulfuric with hydrochloric acid and acetic acids.

The amount of lower-strength hydrochloric acid is selected to provide from 2 to 4 molar equivalents of HCl per mole of thiophenamine.

The amount of concentrated sulfuric acid varies from 0.2 to 2.5 moles per mole of thiophenamine, depending on the amount of water in a wet cake of thiophenamine, and the strength of concentrated hydrochloric acid.

To the mixture of acids is gradually added the thiophenamine with some cooling. If a wet substrate is used, the water content of the wet cake can vary widely, e.g., from 0 to 65 weight percent.

The resulting slurry is cooled to 0°–7° C. and diazotized with one molar equivalent of sodium nitrite dissolved in water. In the course of diazotization, the starting material goes into solution.

To the solution of the diazonium salt is added sulfur dioxide. Its amount of the latter can vary from 1.2 to 5 molar equivalents for each molar equivalent of the diazonium salt. We preferably use about 3 molar equivalents of the sulfur dioxide. This is followed by the addition of cuprous chloride whose amount can vary from 3 to 6 mole percent.

The mixture is warmed to room temperature and the decomposition of the diazonium salt is allowed to proceed to completion.

Alternatively, sulfur dioxide is dissolved in acetic acid containing cuprous chloride, to which is then added the soluton of the diazonium salt in a gradual fashion. The amount of acetic acid is selected to dissolve the required amount of sulfur dioxide. The reacting mixture is also allowed to decompose completely at room temperature.

The resulting suspension of thiophenesulfonyl chloride is cooled and diluted with water. The product is recovered by filtration, washing with water and drying.

The following table is a guide to the examples that follow.

Preparation of Methyl 3-Chlorosulfonylthiophene-2-Carboxylate

| Ex. | Thiophenamine | % HCl Strength | Extra Mineral Acid[a] | % Yield of Product | Wt. % of IV[b] |
|---|---|---|---|---|---|
| 1 | dry | 36 | None | 85.6 | <0.5 |
| 2 | wet | 37 | HCl | 79.0 | <1.0 |
| 3 | wet | 31.5 | None | 56.1 | 16.0 |
| 4 | wet | 31.5 | $H_2SO_4$ | 82.3 | 0.12 |
| 5 | dry | 31.5 | None | 65.1 | 10.8 |
| 6 | dry | 31.5 | $H_2SO_4$ | 82.7 | 0.26 |

[a]Dry hydrogen chloride, conc. $H_2SO_4$, or oleum.
[b]Weight percent of the side-product IV in crude product.

Preparation of Methyl 3-Chlorosulfonylthiophene-2-Carboxylate

EXAMPLE 1

To a mixture of 385 g of concentrated (36 weight percent) hydrochloric acid and 120 mL of glacial acetic acid were added 133 g of 92.4% pure methyl 3-aminothiophene-2-carboxylate while maintaining the internal temperature between 0° and 7° C. To the resulting slurry were slowly added 58 g of sodium nitrite dissolved in 77 mL of water at 0° to 7° C. A solution of the diazonium salt so obtained in one vessel was gradually transferred to a second vessel containing 310 mL of glacial acetic acid, 30 g of concentrated (36 weight percent) hydrochloric acid, 4.8 g of cuprous chloride and 90 g of sulfur dioxide and maintained at 15°–17° C. While the transfer of the diazonium salt was in progress, additional 60 g of sulfur dioxide were slowly being charged subsurface into second vessel. The temperature of the reacting mixture was subsequently allowed to rise to 21° C. The mixture was stirred at room temperature until the evolution of nitrogen was complete. The title sulfonyl chloride was precipitated by the addition of 660 mL of water. It was then filtered, washed with water and dried in vacuo at 40° C. The crude product weighed 179.28 g and was found by high-pressure liquid chromatography to contain 164.94 g of pure sulfonyl chloride for a yield of 85.67% of theory. The crude product contained less than 0.5 weight percent of the side-product of Formula IV.

Example 2

To 49 mL of concentrated hydrochloric acid (36–38%) and 20 mL of acetic acid was added a solution of 45.5 g. of a wet cake of methyl 3-aminothiophene-2-carboxylate (purity of 69.2% and water content of 26.2%) in 40 mL of glacial acetic acid at 0°-5° C. followed by a solution of 15.0 g of sodium nitrite in 21.6 mL of water also at 0°-5° C. To this mixture, kept at 0°-5° C. was slowly added 15 g of dry hydrogen chloride. After stirring the reaction mixture at 0°-5° C. for 30 minutes, 20 g of sulfur dioxide, 10 mL of acetic acid, and 1.0 g of cupric chloride dihydrate were added. The decomposition reaction was carried out at room temperature to completion. The product was precipitated by the addition of 200 mL of cold water at 0°-5° C., the crystals were filtered, washed with water and dried in vacuo under nitrogen at 40° C. The crude product weighed 40.41 g and was found by a high-pressure liquid chromatography to contain 38 g of the title sulfonyl chloride which corresponded to a yield of 79% of theory. The crude product also contained less than 1 wt. % of the side-product of Formula IV.

EXAMPLE 3

To 150.5 g of 31.5% aqueous hydrochloric acid and 180 mL of glacial acetic acid was added gradually, with cooling, 0.40 mole of methyl 3-aminothiophene-2-carboxylate as a wet cake containing 30.5% of water. The resulting slurry was slowly diazotized at 0°-7° C. with 30 g of sodium nitrite dissolved in 43 mL of water. After completion of the addition of sodium nitrite the miXture was stirred at 0°-5° C. for an additional 20-30 minutes. To the diazonium salt solution were added 80 g of gaseous sulfur dioxide, 20 mL of glacial acetic acid, and 4 g of cupric chloride dihydrate. The mixture was stirred at 20°-25° C. until the evolution of nitrogen was complete. The reaction mixture was cooled to 0°-5° C., 330 mL of water was gradually added and the precipitate was stirred at 0°-5° C. for 30 minutes. The solid product was filtered, with water, and dried in vacuo at 40° C. The crude material weighed 71.7 g and was found by high-pressure liquid chromatography to contain 53.9 g of sulfonyl chloride for a yield of 56.1% of theory. The crude material also contained 16.0 wt. % of the side-product having Formula IV.

EXAMPLE 4

In the procedure of Example 3, 36 mL of concentrated sulfuric acid was added dropwise before the starting material at room temperature. The decomposition in the presence of sulfur dioxide was then carried out as described in Example 3. The procedure furnished 85.5 g of a crude product which by analysis contained 79.2 g of the title sulfonyl chloride for a yield of 82.3% of theory The crude material also contained 0.12 wt. % of the side-product of Formula IV.

EXAMPLE 5

In the procedure of Example 3, 67 % of essentially dry methyl 3-aminothiophene-2-carboxylate (94.7% pure and containing 0.1% of water) was used in place of the wet cake. The experiment produced 79.0 g of a crude product which was found by high-pressure liquid chromatography to contain 62.7 g of the title sulfonyl-chloride. This corresponded to a yield of 65.1% of theory. The crude material also contained 10.8 weight % of the side-product having Formula IV.

EXAMPLE 6

In the procedure of Example 3, 67 g of essentially dry methyl 3-aminothiophene-2-carboxylate (94.7% pure containing 0.1% water) was used in place of the wet cake. Also, 26 mL of concentrated sulfuric acid were employed in the manner described in Example 4. The experiment produced 85.7 g of a crude product which was found by high-pressure liquid chromatography to contain 79.6 g of the title sulfonyl chloride. This corresponded to a yield of 82.7% of theory. The crude material also contained 0.26 wt. % of the side-product having Formula IV.

What is claimed is:

1. A process for the preparation of thiophene compounds of Formula I

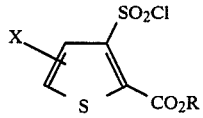

I wherein

R is $C_1$-$C_3$ alkyl; and

X is H, Cl, Br or $CH_3$;

said process comprising:

(a) contacting a thiophenamine of Formula II suspended in excess aqueous hydrochloric acid and a cosolvent selected from acetic, formic or propionic acid with sodium or potassium nitrite, optionally in the presence of a mineral acid booster selected from gaseous hydrochloric acid, concentrated sulfuric acid or oleum, to produce a diazonium salt of Formula III;

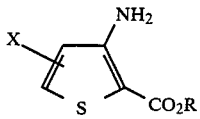

II

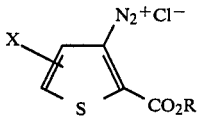

III and, (b) contacting a solution of the diazonium salt of Formula III with sulfur dioxide in the presence of cupric or cuprous chloride, or bromide, to produce said compound of Formula I.

2. The process of claim 1 wherein said cosolvent is acetic acid and the concentration of the aqueous hydrochloric acid is at least 35% by weight.

3. The process of claim 2 wherein R is $CH_3$.

4. The process of claim 3 wherein X is $CH_3$.

5. The process of claim 3 wherein X is H.

6. The process of claim 1 wherein a mineral acid booster is present.

7. The process of claim 2 wherein a mineral acid booster is present.

8. The process of claim 7 wherein the mineral acid booster is present in the amount of 0.1 to 3.5 moles of concentrated sulfuric acid per mole of diazonium salt.

9. The process of claim 7 where the mineral acid booster is present in the amount of 0.2 to 2.5 moles of concentrated sulfuric acid per mole of diazonium salt, R is $CH_3$ and X is H.

* * * * *